(12) United States Patent
Hasirci et al.

(10) Patent No.: US 11,717,821 B2
(45) Date of Patent: Aug. 8, 2023

(54) MICROPATTERNED NUCLEAR DEFORMATION BASED CELLULAR DIAGNOSTIC SYSTEM

(71) Applicants: Vasif Nejat Hasirci, Ankara (TR); Utkan Demirci, Palo Alto, CA (US)

(72) Inventors: Vasif Nejat Hasirci, Ankara (TR); Utkan Demirci, Palo Alto, CA (US); Menekse Ermis Sen, Ankara (TR); Derya Akkaynak, Ankara (TR)

(73) Assignees: Vasif Nejat Hasirci, Ankara (TR); Utkan Demirci, Palo Alto, CA (US)

( * ) Notice: Subject to any disclaimer, the term of this patent is extended or adjusted under 35 U.S.C. 154(b) by 1131 days.

(21) Appl. No.: 16/346,197

(22) PCT Filed: Oct. 6, 2017

(86) PCT No.: PCT/TR2017/050481
§ 371 (c)(1),
(2) Date: Apr. 30, 2019

(87) PCT Pub. No.: WO2018/182556
PCT Pub. Date: Oct. 4, 2018

(65) Prior Publication Data
US 2019/0291105 A1     Sep. 26, 2019

(30) Foreign Application Priority Data
Oct. 31, 2016   (TR) ................................ 2016/15290

(51) Int. Cl.
*B82Y 40/00*       (2011.01)
*B01L 3/00*        (2006.01)
*G06T 7/00*        (2017.01)
*C12M 1/00*        (2006.01)
*G01N 33/48*       (2006.01)
*B82Y 5/00*        (2011.01)
*B82Y 30/00*       (2011.01)

(52) U.S. Cl.
CPC ....... *B01L 3/502715* (2013.01); *B01L 3/5088* (2013.01); *B01L 3/502707* (2013.01); *C12M 23/00* (2013.01); *C12M 23/20* (2013.01); *G01N 33/48* (2013.01); *G06T 7/0012* (2013.01); *B01L 2200/0663* (2013.01); *B01L 2300/0819* (2013.01); *B01L 2300/123* (2013.01); *B82Y 5/00* (2013.01); *B82Y 30/00* (2013.01); *B82Y 40/00* (2013.01); *G01N 2800/7028* (2013.01)

(58) Field of Classification Search
CPC ......... B01L 3/502715; B01L 3/502707; G06T 7/0012; B82Y 40/00
See application file for complete search history.

(56) References Cited

U.S. PATENT DOCUMENTS
2010/0303722 A1   12/2010   Jin et al.

FOREIGN PATENT DOCUMENTS
WO        2013162482 A1   10/2013

OTHER PUBLICATIONS

K. Nagayama et al., Mechanical Trapping of the Nucleus on Micropillared Surfaces Inhibits the Proliferation of Vascular Smooth Muscle Cells but not Cervical Cancer HeLa Cells, 48 J. Biomech. 1796-1803 (2015).*
Kazuaki Nagayama et al: "Mechanical trapping of the nucleus on micropillared surfaces ,inhibits the proliferation of vascular smooth muscle cells but not cervical cancer HeLa cells", Journal of Biomechanics, Jul. 16, 2015, pp. 1796-1803, vol. 48, No. 10, ISSN: 0021-9290, DOI: 10. 1016/j .jbiomech.2015.05 004, p. 1797, col. 1, paragraph 2.2-col. 2, paragraph 2.;figures 1,3.
Yo Tanaka et al: "Demonstration of a PDMS-based bio-microactuator using cultured cardiomyocytes to drive polymer micropillars", Lab on a Chip, Jan. 1, 2006, p. 230, vol. 6, No. 2, ISSN: 1473-0197, DOI: 10.1039/b512099c, p. 231, col. 2, paragraph 2-p. 232, col. 2, paragraph 1; figure 1.
Vernella Vickerman et al: "Design,fabrication and implementation of a novel multi-parameter control microfluidic, platform for three-dimensional cell culture and real-time ,imaging", Lab on a Chip, Jan. 1, 2008, p. 1468, vol. 8, No. 9, ISSN: 1473-0197, D0I : 10.1039/b802395f, p. 1469, col. 2, paragraph 2-p. 1472; figure 2.
Laurene Aoun et al. "Microdevice arrays of high aspect ratio poly(dimethylsiloxane) pillars for the investigation of multicellular tumour spheroid mechanical properties", Lab on a Chip, Jan. 1, 2014, p. 2344, vol. 14, No. 13, ISSN: 1473-0197, DOI: 10.1039/c41c00197d, p. 2345, col. 2, paragraph 1-p. 2346, col. 1, paragraph 2; figure 1.
Yi-Tsung Lu et al: "NanoVelcro Chip for CTC enumeration in prostate cancer patients", Methods, Dec. 1, 2013, pp. 144-152, vol. 64, No. 2, ISSN: 1046-2023, DOI: 10.1016/j.ymeth.2013.06.019, p. 145, col. 2, paragraph 2; figures 1,3,4.

* cited by examiner

*Primary Examiner* — Randy Boyer
(74) *Attorney, Agent, or Firm* — Bayramoglu Law Offices LLC

(57) ABSTRACT

A diagnostic method for a detection of a nuclear deformation based a cellular differentiation includes the following steps: preparing nano/micropatterned surfaces; performing a cell seeding on the nano/micropatterned surfaces; imaging; analyzing nuclear deformations of a single cell and a cell population with an algorithm method.

12 Claims, 5 Drawing Sheets

MICROPATTERNED NUCLEAR DEFORMATION BASED CELLULAR DIAGNOSTIC SYSTEM

CROSS REFERENCE TO THE RELATED APPLICATIONS

This application is the national phase entry of International Application No. PCT/TR2017/050481, filed on Oct. 6, 2017, which is based upon and claims priority to Turkish Patent Application No. 2016/15290, filed on Oct. 31, 2016, the entire contents of which are incorporated herein by reference.

TECHNICAL FIELD

This invention is about a cellular diagnostic system which is composed of micro/nano patterned surfaces that can be integrated into a microfluidics device which reveals the nuclear shape deformability of the cells; which can be imaged with the help of an optical system and can be quantified with a software algorithm.

BACKGROUND

There are two device categories readily available in the market about cytological and histological diagnosis. FocalPoint (Becton Dickinson) and ThinPrep (Hologic) devices are in cytological specimens category and can analyze PAP cytology specimens for cervical cancer diagnosis. These devices prepare smears of the sample on a microscope slide, stain the samples and using a special algorithm analyze the difference in morphology and staining of the squamous and glandular epithelial cells using widefield light microscopy.

Other automated diagnostic devices in the market include image based detection software that work with paraffin/cryo embedded sectioned and stained samples imaged using widefield light microscopy.

Current technical problems arise from the fact that these methods are static, which means they can only give information about the condition of cells at the moment of fixation, embedding or staining. These sectioning and cytology techniques detect morphological changes resulting from the disease. The method of this invention allows detection of changes in nuclear elasticity of the cells caused by the conditions and makes these changes in the nuclear elasticity visible and detectable. Introduction of the nano/micropatterned interface, the invention allows cells to show properties that were otherwise hidden allowing the detection and diagnosis of disease (e.g. cancer).

SUMMARY

The invention has advantages over the current techniques due to the properties mentioned below:
- Nano/micropatterned polymer surface allows the determination of the extent of nuclear deformation of the cells due to the following factors:
  - Micropillar size,
  - Micropillar height,
  - Micropillar shape/geometry,
  - Interpillar distance,
- Detecting differences between cells using the nuclear elasticity property,
- Devising a single cell and population-wise quantification system using the differences in the nuclear elasticity of cells.
- Devising a single cell and population-wise quantification system using the changes in nuclear elasticity of cells in disease conditions.
- Combination of nano/micropatterned substrates and microfluidics chip to develop a nuclear deformation based disposable diagnostic kit.
- Presence of an algorithm which detects nuclear deformation of the cells (by combining rectangularity and circular variance analysis to calculate a deformation score).

DEFINITIONS OF THE COMPONENTS THAT FORM THE INVENTION

Figure 1A:
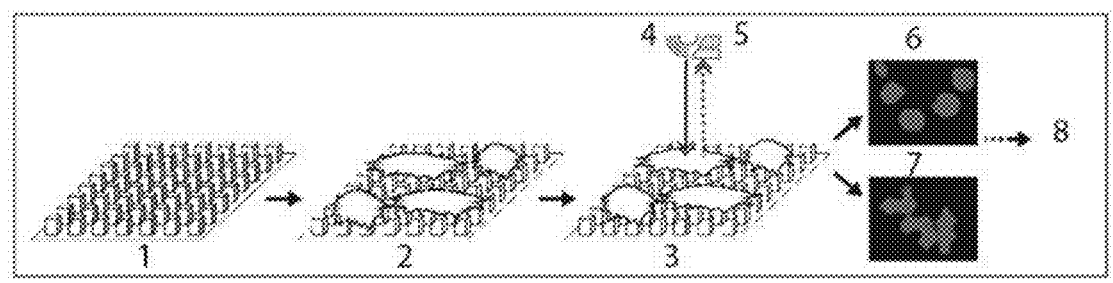
FIG. 1a: Preparation of nano/micropatterned surfaces and analysis using nuclear deformation method.

1. Processor
2. Detector
3. Emitted light
4. Dicroic
5. Excitation light
6. Light source
7. Objective
8. Microfluids chip

DETAILED DESCRIPTION OF THE EMBODIMENTS

The invention described here, uses nano/micropatterned surfaces to force nuclei of the cell; which otherwise have similar morphology under the light microscope; to deform and accentuate minute differences in nuclear deformability and elasticity of the cell nucleus. The algorithm specifically designed to detect changes in the nuclear shape quantifies the extent of nuclear deformation. Using this quantification data, a diagnostic tool is devised. All the steps of the invention can work with live cells and does not require fixation which allows employing the same cells/tissue for further analysis (genetic analysis, etc.).

The invention includes nano/micro pillar surfaces prepared with defined height, dimension, and interpillar spacing, seeding these surfaces with cells and deformation of the cell nuclei. The extent of the nuclear deformation of the cell nucleus depends on disease state of the cell, hydrophobicity of the surface and distribution and size of the micropillars. The algorithm described in the invention quantifies the extent of nuclear deformation and generates a deformation score for diagnosis.

The cellular diagnostic system described in the invention has the following steps for diagnosis method:

a) Preparation of Nano/Micropatterned Surfaces:

The nano/micropatterned surfaces are prepared using methods like lithography, molding or hot embossing. Surfaces are made from biodegradable or nonbiodegradable polymers (ex: poly(lactic acid-co-glycolic acid) (PLGA), polylactic acid (PLA), poly(methyl methacrylate) (PMMA), poly(hydroxyethyl methacrylate) (PHEMA), polyacrylamide (PAAm), etc.).

Preparation steps of the nano/micropatterned surfaces are:
1) Silicon wafer produced by photolithography or ion beam lithography or laser lithography is placed into a container,
2) Poly(dimethyl siloxane) (PDMS) is poured onto the silicon wafer and cured in the oven,
3) PDMS mold solidified during curing and peeled off from the silicon wafer,
4) PDMS replica is used as a frame, and biodegradable or nondegradable polymer solution is poured into it, and solvent is evaporated.
5) Steps 2-4 can be performed without the use of a intermediary silicone mold or by hot embossing method.

Polymers that require chemical or photocrosslinking have an additional crosslinking step for nano/micropatterned surface preparation.

Nano/micropatterned array aims to deform cell nuclei. It includes nine surfaces. The surface is decorated with square prism micropillars. Micropillars dimensions are between 2-20 µm (Ex: A square prism micropillar with 4 µm edge and 4×4 µm cross sectional area). On each surface interpillar distance of the micropillars is different. Interpillar distances range between 2-20 µm (Ex: 4×4 micropillars separated from one another by an 8 µm spacing).

Nano/micropatterned silicon chips are prepared by photolithography, ion beam lithography or laser lithography methods. These silicon chips are designed to allow either duplicating the surface features directly or through the use of an intermediate mold (silicone).

There are two methods to produce nano/micropatterned test surfaces: (A) directly from silicon chips, (B) by preparing a secondary silicone mold. These molds (A, B) can be employed several ways: (i) using a polymer solution and solvent evaporation, (ii) hot embossing with a pre-made polymer film, (iii) UV crosslinking a polymer solution or (iv) chemical cross-linking.

Nano/micropatterned and biocompatible surfaces are sterilized with any heat free methods (gamma irradiation, UV, ethylene oxide).

b) Cell Seeding:

After the succession of the sterilization procedure cells are seeded on the nano/micropatterned surface and cultured from 4 h to 21 d depending on the choice of testing. Cells can be seeded onto the surface in a growth medium as single cell types or mixed populations. The nuclei of the cells deform according to the source of their native tissue, stemness or differentiation states or disease/health conditions.

c) Imaging:

Nano/micropatterned surfaces with the cells on top of them are prepared for imaging. If the samples are chosen to be fixed; alcohol, paraformaldehyde, formaldehyde or glutaraldehyde can be used for the fixing process. Afterwards, they are stained with a nucleus or DNA dye. If the samples are not fixed, the cell is stained with the appropriate live cell dyes in the growth medium. Dyes can be selected according to the configuration of the microscope used. Samples stained with the dye either after fixation or in alive are imaged with a microscope with fluorescent light source. This microscope can be upright or inverted. Images can be acquired in RGB or gray scale. For fast processing, original images are 30% resized. If the image is in RGB, the channel (red, green or blue) with nucleus/DNA stain is extracted and converted to gray scale.

d) Analysis:

An algorithm is developed as a part of the invention. This algorithm performs nuclear deformation analysis for individual cells and cell populations.

Working principle of the nuclear deformation algorithm mentioned in the invention is as follows:

Reading the RGB format image,
Converting it to gray scale,
Detecting all the cell nuclei in the image,
Excluding nuclei with low signal intensity,
Getting the binary images using the Otsu method,
Excluding nuclei at the four borders of the image (since these nuclei are not completely in the image, they may cause wrong analysis results),
Excluding very large (larger than 1% of the length or width of the image) and very small (smaller than 50 pixels) nuclei,
Detecting cell nuclei going through cell division with watershed transformation and excluding cell in mitosis,
After quality control, smoothing the remaining cell nuclei images by using a Gaussian filter (n=5, σ=10) to even rough pixel edges,
Applying morphological to eliminate any artefacts,
Rotating each nuclei by orienting its major axis to the y-axis, and ensuring the centroid was always on the right side of the major axis,
For scale invariance, scaling each nuclei image longest dimension to 64 pixels while preserving aspect ratio,
Cleaning the noise (low cut filter, morphological opening, median filter)
Excluding nuclei that occupied 100% of their bounding boxes, which were clearly artefacts,
Calculating the rectangularity (R) of the nucleus:

$$R = \left| \frac{\pi}{4} - \frac{A_{cell}}{A_{bounding\ box}} \right|$$

Calculating the circle variance (CV): is the ratio of the standard deviation of the radial Euclidean distance (di) between the centroid of a cell to each of its N boundary points, to that of their mean, where:

$$\mu_R = \frac{1}{N}\sum_{i=1}^{N-i} d_i,\ \sigma_R = \sqrt{\frac{1}{N}\sum_{i=1}^{N-1}(d_i - \mu_R)^2},\ CV = \frac{\sigma_R}{\mu_R}$$

Calculating the deformation score (DS)

Figure 3:
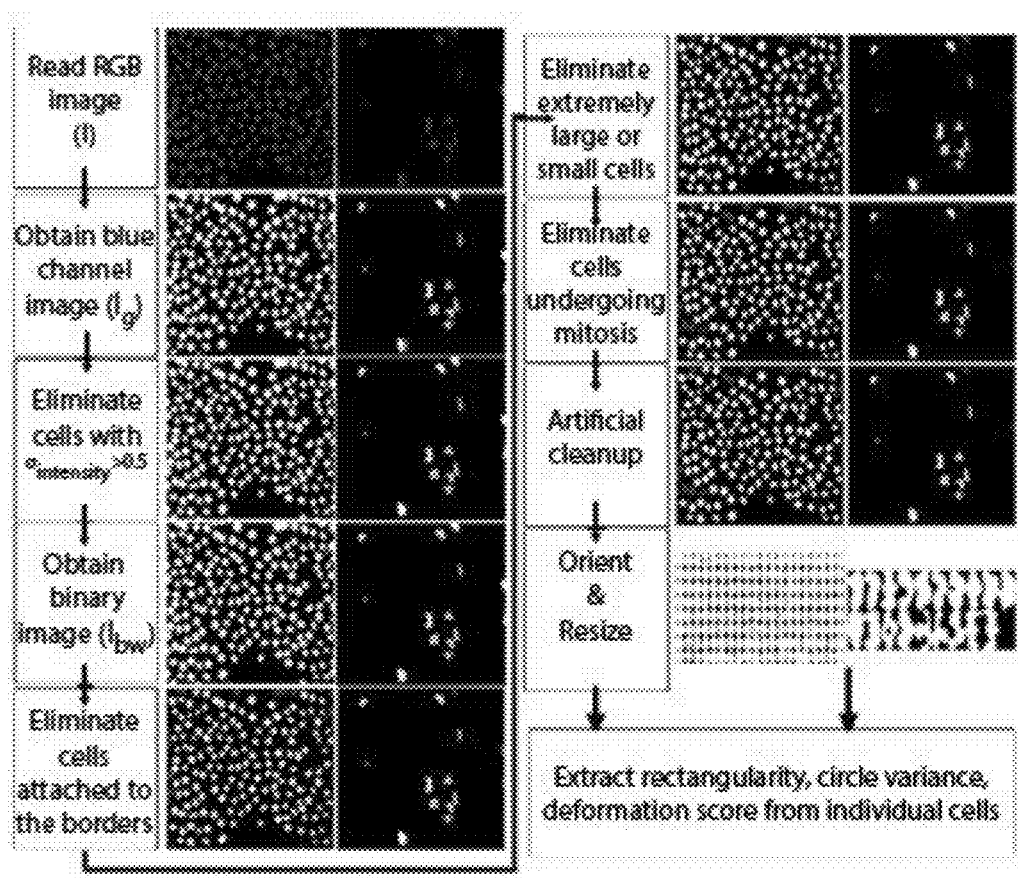
FIG. 3: Working principle of the algorithm used in the invention and steps.
Figure 4:
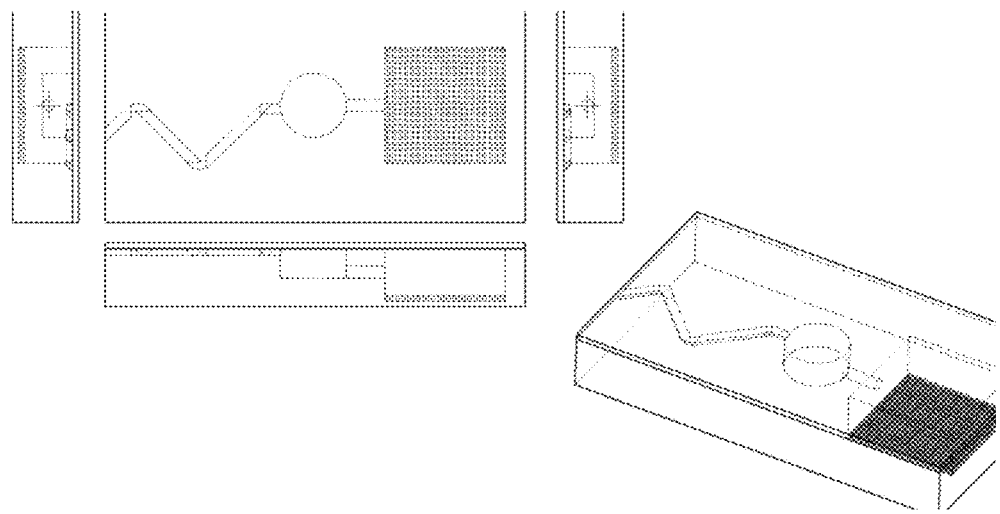
FIG. 4: Design of the nano/microfluidics chip.
Figure 5:
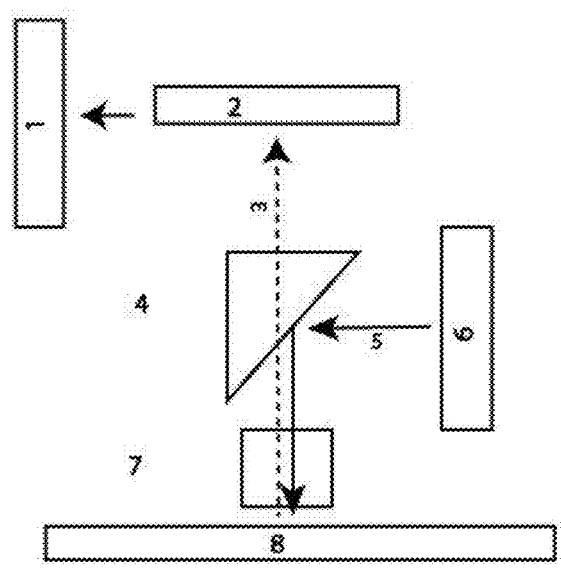
FIG. 5: Working principle of the integrated nano/micropatterned nano/microfluidics chip and imaging system.
Figure 6:
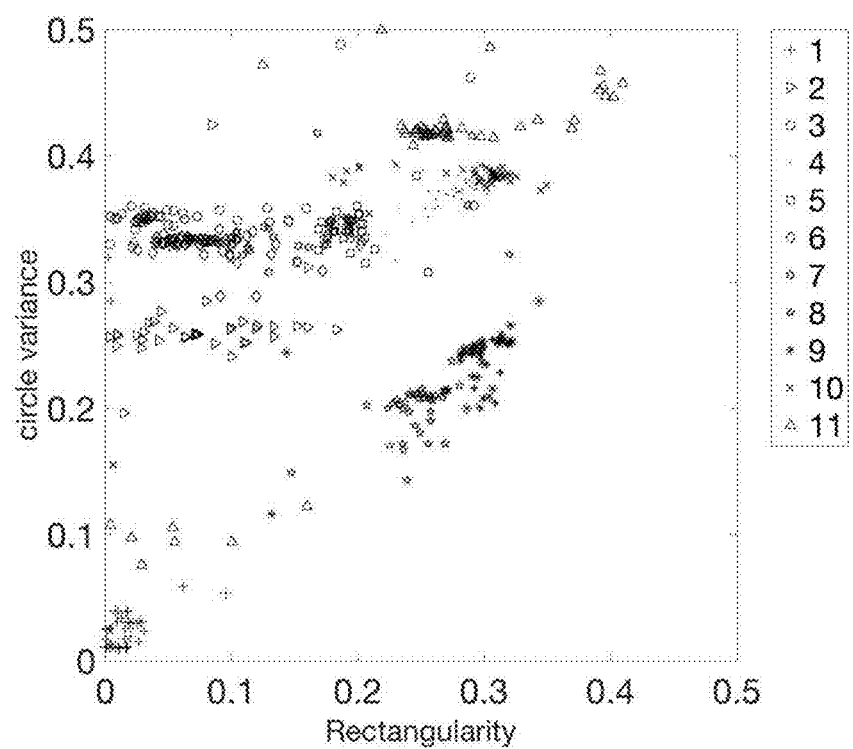
FIG. 6: Graph of the rectangularity and circle variance.

The nano/micropatterned surfaces are integrated into a microfluidics chip to obtain a disposable diagnostic system product with a shelf life. This microfluidics chips design includes channels for feeding cells and growth media into the nano/micropatterned reservoir and output channels for excess fluids. DNA dye reaches to the cells when the growth media dissolves the dye in the dye chamber. Cells are stained alive with the dye, and nuclear deformations become visible. Nano/micropatterned surface integrated microfluidics chip can be imaged with the desired microscopy tool (any microscope sensitive to fluorescence). The dye is excited with the excitation wavelength of the dye, and the emitted light goes through a dichroic mirror to meet the detector. After obtaining the digital image analysis is performed according to the FIG. 3.

After the processing steps mentioned above, two parameters were calculated using the image of each cell nucleus:

1—Rectangularity (R) is defined as the ratio of the area of a cell to that of the minimum rectangle that encompasses it, and is a measure of compactness. Rectangularity of an ideal unit circle is $\pi/4$. When this value is subtracted from the calculated value rectangularity is calculated as '0' for the unit circle:

$$R = \left| \frac{\pi}{4} - \frac{A_{cell}}{A_{bounding\ box}} \right|$$

2—Circle variance: Circle variance (CV) is a measure of how much a shape deviates from an ideal unit circle, obtained by dividing the standard deviation of the distances between the centroid of the shape to points on its boundaries, by that of their mean. Circle variance is zero for an ideal unit circle as all distances are equal to the radius of the circle, with their standard deviation being 0, and mean 1.

$$\mu_R = \frac{1}{N}\sum_{i=1}^{N-i} d_i,\ \sigma_R = \sqrt{\frac{1}{N}\sum_{i=1}^{N-1}(d_i - \mu_R)^2},\ CV = \frac{\sigma_R}{\mu_R}$$

The nano/micropatterned diagnostics chip that quantifies deformation of the cell nuclei has the following properties:

Nano/micropatterned surface can be chemically modified (biopolymers, synthetic polymers, ceramic materials, metals, etc.) according to the purpose (cell type, disease, sample type, etc.), The diagnostic chip will perform the quantification analysis with a surface having pillar height between 100 nm-20 μm, dimensions between 100 nm-20 μm and interpillar spacing between 1-20 μm, Nano/micropatterns can have isotropic or anisotropic distribution, Base and micropillars can be made from different materials, Surface wettability (hydrophobicity and hydrophilicity) can be modified with a chemical surface modification or changing the micropillar density, The nano/micropatterned surface can be integrated into a microfluidics chip for imaging.

Example 1

Calculation of Surface which Supplies the Most Nucleus Deformation on the Micropatterned Chip by Using Algorithm.

Figure 1B:
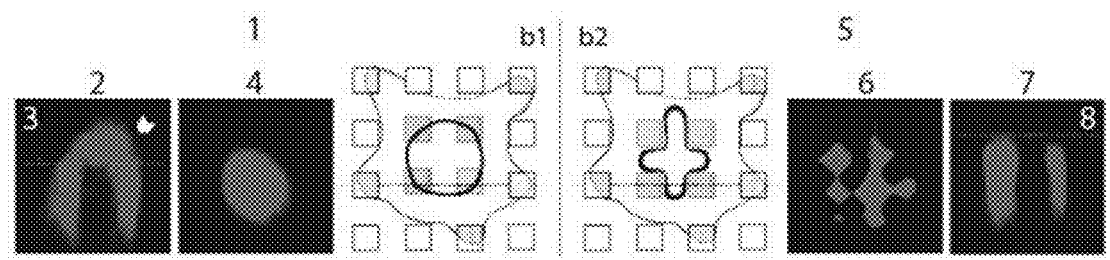
FIG. 1b: Imaging the deformations.
Figure 2:
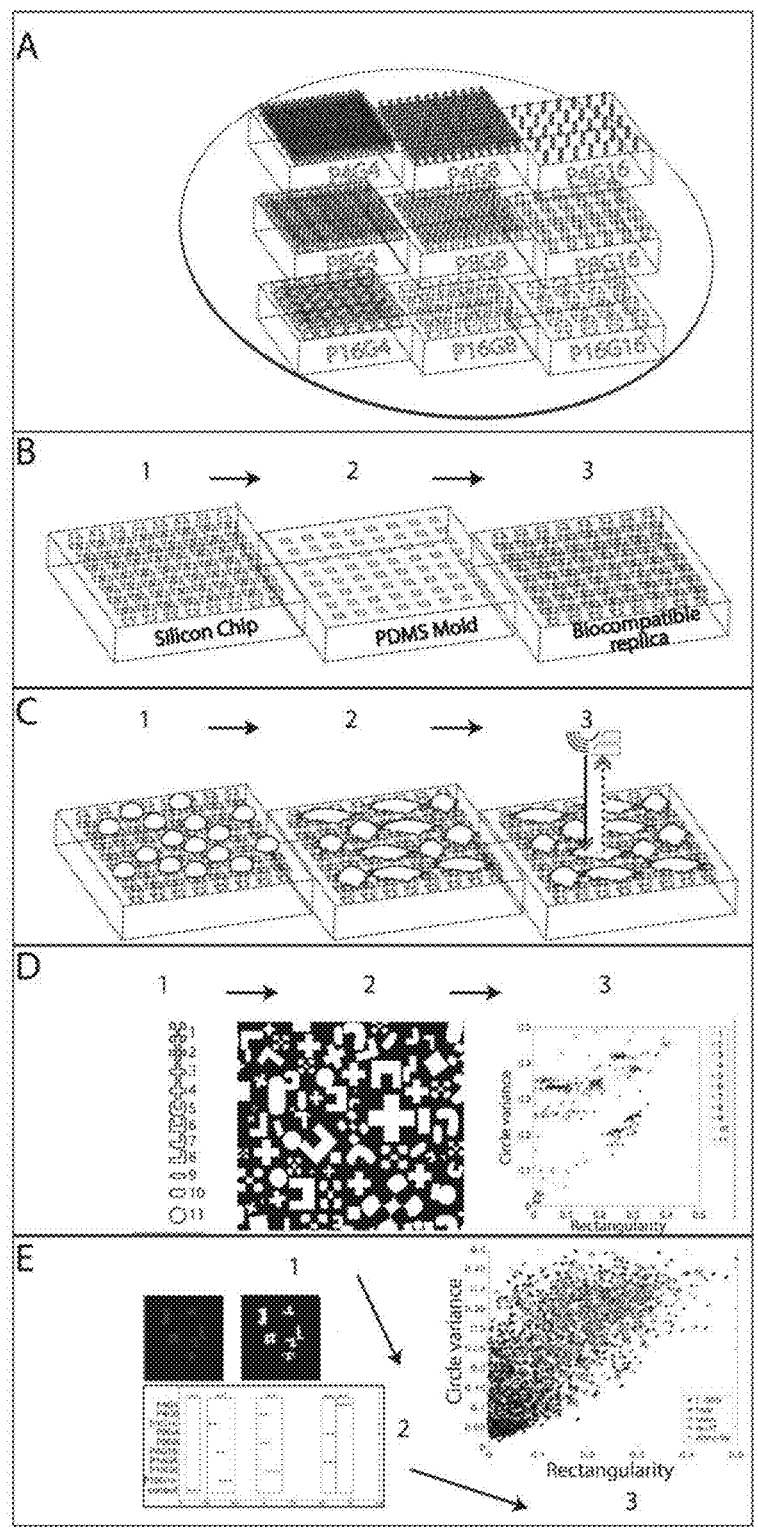
FIG. 2: The working flowchart of the quantification of nuclear deformation of the cells on nano/micropatterned substrates.

Using only the P4G4 surface, which induced the highest level of nuclear deformation, we evaluated the diagnostic performance of our software algorithm using six different cell types: L929, Saos-2, hOB, MCF-7, and SH-SY5Y. To accurately distinguish undeformed cell populations from deformed ones, we developed a finer scoring rubric than the one we used for surface selection. We defined a deformation score (DS), which combined how much the shape of a cell deviated from an ideal circle with whether it stayed more compact (e.g., like an ellipse) or obtained a bent shape (e.g., the shape of the letter "L"). To derive the parameters of this rubric, we created a database of synthesized cell nuclei. We designed 11 main cell templates (i.e., variants of deformed cells) we expected to see on cells on the P4G4 surface, with 50 examples of each (550 cells total) (FIG. 3a1). Each cell had a random orientation and scale, and was randomly filtered using Pinch, Twirl, Wave and Ripple filters in Photoshop (Adobe, Inc.) to distort and add noise, simulating actual data. Then, based on the distribution of these test data in the two-dimensional rectangularity and circle variance space, we performed gating to obtain the five regions. The regions were characterized as follows:

R1 ($R_1$, CV1≤0.1, 0.1): no deformation,

R2 (0.1, 0.1<$R_2$, CV2≤0.2, 0.2): low deformation-more compact,

R3 (0.2, 0<$R_3$, CV3≤0.5, 0.3) low deformation-less compact,

R4 (0, 0.3<$R_4$, CV4≤0.2, 0.5) high deformation-more compact and

R5 (0.2, 0.3<$R_5$, CV5≤0.5, 0.5) high deformation-less compact (FIG. 3a1).

Following this, we assigned weights to each cell based on the region it fell in $w_i$=1:5, where i=R1 to R5. These weights indicate the deformation score at an individual cell level and are used as input to calculate population-level deformation score as follows:

$$DS = w*p'/100, \quad (5)$$

where p' is a vector representing the percentage of cells that fall in each of the regions R1-R5. An undeformed cell population would have minimally or none deformed cells (e.g., theoretically, 100% of its cells would fall gating area #1 and receive the minimum score of DS=1. Similarly, a deformed cell population would have cells that deform extensively (e.g., theoretically 100% of its cells should fall in the gating area #5) and receive the maximum score of DS=5. Based on this convention, the 'undeformed' and 'deformed' classes in the Surface Selection section correspond to DS≤3 and DS>3, respectively. We adopted this threshold as the cut-off between undeformed and deformed populations.

What is claimed is:

1. A diagnostic method for a detection of a nuclear deformation based a cellular differentiation, comprising the following steps:
   a) preparing micropatterned surfaces:
      1) Placing a silicon wafer produced by photolithography or an ion beam lithography into a container,
      2) pouring poly(dimethyl siloxane) (PDMS) onto the silicon wafer and curing the silicon wafer with the PDMS in an oven,
      3) solidifying a PDMS mold during curing, and peeling off the PDMS mold from the silicon wafer,
      4) using a PDMS replica as a frame, and
         i) pouring a biodegradable polymer solution or a nondegradable polymer solution into the PDMS replica, and evaporating a solvent, or
         ii) hot embossing the PDMS replica with a pre-prepared polymer film;
      5) performing a crosslinking step on polymers requiring a chemical or photocrosslinker;
   b) performing cell seeding on the nano/micropatterned surfaces;
   c) imaging:
      putting the micropatterned surfaces with cells on a top as samples for an imaging,
      staining each of the samples with a nucleus dye or a DNA dye, and imaging each sample with a confocal laser scanning or a fluorescence microscope;

d) analyzing nuclear deformations of a single cell and a cell population with an algorithm method comprising the following steps:

reading an image in a RGB format, converting the RGB format to a gray scale, detecting cell nuclei in the image, getting binary images using the Otsu method, excluding cell nuclei at four borders of the binary images, excluding nuclei that are larger than 1% of the length and width of the image, and nuclei that are smaller than 50 pixels, detecting cell nuclei going through a cell division, and excluding cell in mitosis, smoothing remaining cell nuclei images by using a Gaussian filter to even rough pixel edges, applying morphological opening to eliminate any artefacts, rotating each nucleus by orienting a major axis of each nucleus to a y-axis, and ensuring a centroid is always on a right side of the major axis, for a scale invariance, scaling a longest dimension of an image of each nucleus to 64 pixels while preserving an aspect ratio, cleaning a noise with a low cut filter, and/or a morphological opening, and/or a median filter, excluding nuclei that occupy 100% of bounding boxes, and nuclei that are clearly artefacts, calculating a rectangularity (R) of the nucleus, where $A_{cell}$ is the area of the nucleus identified, and $A_{boundingbox}$ is the area of the smallest rectangle that encompasses this nucleus:

$$R = \left| \frac{\pi}{4} - \frac{A_{cell}}{A_{bounding\,box}} \right|$$

calculating a circle variance (CV), where circle variance (CV) is the ratio of the standard deviation ($\sigma_R$) of the radial Euclidean distance ($d_i$) between the centroid of a cell to each of its N boundary points, to that of their mean ($\mu_R$):

$$\mu_R = \frac{1}{N} \sum_{i=1}^{N-i} d_i,$$

$$\sigma_R = \sqrt{\frac{1}{N} \sum_{i=1}^{N-i} (d_i - \mu_R)^2},$$

$$CV = \frac{\sigma_R}{\mu_R}$$

calculating a deformation score (DS), where the score is assigned based on a rubric calibrated for five regions in the Cartesian plane having coordinates of the corners of each region as follows:

(R1) Region1 (R, CV≤0.1,0.1): no deformation, (R2) Region2 (0.1, 0.1<R, CV→0.2, 0.2), low deformation, more compact, (R3) Region3 (0.2, 0<R, CV→0.5, 0.3) low deformation, less compact, (R4) Region4 (0,0.3<R, CV→0.2, 0.5) high deformation, more compact, (R5) Region5 (0.2, 0.3<R<0.5,0.5) high deformation, less compact, and after defining the regions R1 to R5, weights are assigned to each nucleus based on the region it falls in: $w_i$=1:5, where i=R1 to R5, these weights indicate the deformation score at an individual cell level and are used as input to calculate population-level deformation score as follows: DS=* w p'/100, where p' is a vector representing the percentage of cells that fall in each of the regions R1-R5.

2. The diagnostic method according to claim 1, wherein the cells are cultured after the cell seeding from 4 hours to 21 days.

3. The diagnostic method according to claim 1, wherein the cells are seeded as the single cell or the cell population.

4. The diagnostic method according to claim 1, wherein the samples are imaged after a fixation or in an alive state.

5. The diagnostic method according to claim 4, wherein the samples are fixed by alcohol, paraformaldehyde, formaldehyde or glutaraldehyde.

6. The diagnostic method according to claim 1, wherein the micropatterned surfaces are made from a biodegradable polymer or a non-biodegradable polymer.

7. The diagnostic method according to claim 1, wherein the micropatterned surfaces are made using the PDMS mold and a solvent casting and evaporation of the biodegradable polymer solution and the nonbiodegradable polymer solution.

8. The diagnostic method according to claim 1, wherein the micropatterned surfaces are made using the silicon wafer as a mold and solvent casting and evaporation of the biodegradable polymer solution and the non-biodegradable polymer solution.

9. The diagnostic method according to claim 1, wherein the micropatterned surfaces are made using the PDMS mold and hot embossing of the pre-prepared polymer film.

10. The diagnostic method according to claim 1, wherein the micropatterned surfaces are made using the silicon wafer as a template and hot embossing of the pre-prepared polymer film.

11. The diagnostic method according to claim 1, wherein the micropatterned surfaces are made from poly(lactic acid-co-glycolic acid) (PLGA), or polylactic acid (PLA), poly(methyl methacrylate) (PMMA), poly(hydroxyethyl methacrylate) (PHEMA), or polyacrylamide (PAAm).

12. The diagnostic method according to claim 1, wherein the micropatterned surfaces are sterilized with gamma irradiation, UV or ethylene oxide.

* * * * *